(12) United States Patent
Grafton et al.

(10) Patent No.: US 6,517,564 B1
(45) Date of Patent: Feb. 11, 2003

(54) BIOABSORBABLE TISSUE TACK WITH OVAL-SHAPED HEAD AND METHOD OF TISSUE FIXATION USING SAME

(75) Inventors: R. Donald Grafton, Naples, FL (US); David J. Chao, San Diego, CA (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 09/495,816

(22) Filed: Feb. 2, 2000

Related U.S. Application Data

(60) Provisional application No. 60/118,228, filed on Feb. 2, 1999, and provisional application No. 60/125,781, filed on Mar. 23, 1999.

(51) Int. Cl.$^7$ .............................................. A61B 17/04
(52) U.S. Cl. ........................... 606/213; 606/72; 606/77
(58) Field of Search .............................. 606/72, 73, 77, 606/232

(56) References Cited

U.S. PATENT DOCUMENTS

| | | |
|---|---|---|
| 204,913 A | 6/1878 | Pratt |
| 3,166,072 A | 1/1965 | Sullivan, Jr. ................. 128/334 |
| 4,743,257 A | 5/1988 | Törmälä et al. ............... 623/16 |
| 4,873,976 A | 10/1989 | Schreiber ..................... 128/334 |
| 4,884,572 A | 12/1989 | Bays et al. .................. 128/334 |
| 4,895,148 A | 1/1990 | Bays et al. .................. 606/213 |
| 4,924,865 A | 5/1990 | Bays et al. .................... 606/77 |
| 4,968,317 A | 11/1990 | Törmälä et al. ............... 606/77 |
| 4,976,715 A | 12/1990 | Bays et al. .................... 606/77 |
| 5,059,206 A | 10/1991 | Winters ........................ 606/77 |
| 5,129,906 A | 7/1992 | Ross et al. .................... 606/77 |
| 5,246,441 A | 9/1993 | Ross et al. .................... 606/53 |
| 5,261,914 A | 11/1993 | Warren ......................... 606/73 |
| 5,380,334 A | 1/1995 | Torrie et al. ................. 606/104 |
| 5,400,805 A | 3/1995 | Warren ....................... 128/898 |
| 5,522,843 A | 6/1996 | Zang ........................... 606/232 |
| 5,720,766 A | 2/1998 | Zang et al. ................... 606/232 |
| 6,007,539 A | 12/1999 | Kirsch et al. .................. 606/75 |

FOREIGN PATENT DOCUMENTS

| | | |
|---|---|---|
| EP | 0611557 | 8/1994 |
| WO | 9726028 | 7/1997 |
| WO | WO 9726028 | 7/1997 |

OTHER PUBLICATIONS

Speer et al., "An Arthroscopic technique for anterior stabalization of the shoulder with a bioabsorbable tack," *Journal of Bone and Joint Surgery*, Vo. 78–A, No. 12, pp. 1801–07 (Dec. 1996).
"Biofix® Meniscus Arrow" brochure, Biocon, Ltd.
"The Meniscus Arrow" brochure, Bionx, Inc.
"Bankart Tack", brochure, Bionx Implants, Inc., 1998.
W.Z. Burkhead, M.D., "Surgical Technique for Contour Labrol Nail", Bionx Implants, Inc.
"Contack™ Labral Anchor", brochure, Innovasive Devices, Inc., 1999.
Brochure on "Surgical Technique for Suretac" (undated).
Linvatec, "BioStinger™ Bio–Absorbable Meniscal Fixation" Surgical Technique and Special Features (undated).

*Primary Examiner*—Gary Jackson
(74) *Attorney, Agent, or Firm*—Dickstein Shapiro Morin & Oshinsky, LLP

(57) ABSTRACT

A bioabsorbable, cannulated tissue tack having an oblong head is used in sutureless soft tissue fixation to bone, particularly in arthroscopic shoulder surgery. Slotted ribs are formed along the shaft of the tack. Repair of the glenohumeral joint is performed by installing the tack through a hole formed through the soft tissue of the labrum and into the cancellous bone of the glenoid rim. Aligning the oblong head of the tack lengthwise along the glenoid rim provides a low profile that avoids articular impingement on the tack head.

10 Claims, 5 Drawing Sheets

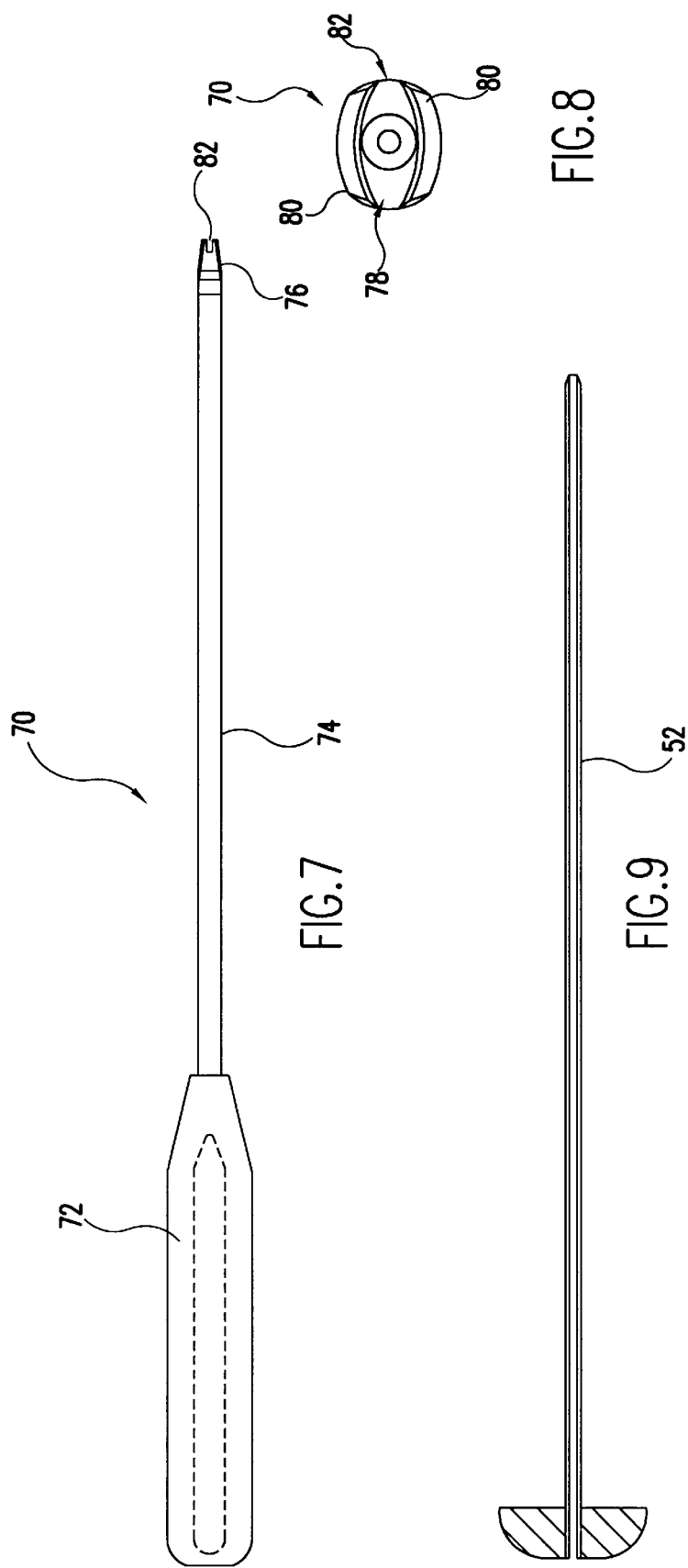

BIOABSORBABLE TISSUE TACK WITH OVAL-SHAPED HEAD AND METHOD OF TISSUE FIXATION USING SAME

This application claims the benefit of U.S. Provisional Application Serial No. 60/118,228 filed Feb. 2, 1999 and U.S. Provisional Application Serial No. 60/125,781 filed Mar. 23, 1999, the entire disclosures of which are incorporated herein by reference.

BACKGROUND OF THE INVENTION

1. Field of the Invention

The present invention relates to sutureless fixation of tissue to bone. More specifically, the present invention relates to a bioabsorbable cannulated tissue tack with an angled or straight oval-shaped head for sutureless tissue fixation in the shoulder.

2. Description of the Related Art

When soft tissue tears away from bone, reattachment becomes necessary. Various fixation devices, including sutures, screws, staples, wedges, and plugs have been used in the past to secure soft tissue to bone. More recently, various types of threaded suture anchors have been developed.

The known suture anchors generally require that the surgeon tie knots in the suture to secure tissue to the bone. Tying surgical knots is tedious and time consuming. It would be preferable to be able to secure the soft tissue to the bone in one step without having to tie knots.

Accordingly, a need exists for a bioabsorbable anchor for soft tissue fixation that can be installed to secure tissue easily and effectively without sutures. A need also exists for a soft tissue fixation device having a low profile configuration particularly suited for reattachment of tissue to the glenoid rim.

SUMMARY OF THE INVENTION

The present invention overcomes disadvantages of the prior art and fulfills the needs discussed above by providing a bioabsorbable tissue tack for sutureless fixation of soft tissue to bone. The tissue tack is cannulated and has a tack shaped configuration. The head of the tack is oblong to provide a low-profile, and is mounted on a cannulated shaft. The head is mounted at a perpendicular angle to the shaft, or, alternatively, at an anatomic angle.

Preferred indications for the tissue tack of the present invention include arthroscopic or open repair of glenohumeral joint pathologies. These include reattachment of the glenoid labrum or inferior glenohumeral ligament in patients with primary or recurrent anterior dislocation or subluxation of the shoulder, in association with adequate post-operative immobilization.

The oblong shape of the tack head provides a narrow profile in one direction to allow head alignment along the glenoid rim. In a preferred embodiment, the heads are oval or elliptical in shape, although a rectangular or diamond oblong shape, for example, also could be used. The oblong head of the installed tack is aligned with the glenoid rim in shoulder repairs, for example, to present a low profile that prevents contact of the tack with articular surfaces.

Advantageously, according to an alternative embodiment, the oblong head is disposed on the shaft in an angled configuration for situations in which the insertion portal of the tack is not perpendicular to the glenoid rim. Accordingly, both of the extended sides of the oblong head will sit flush with the tissue along the glenoid rim.

BRIEF DESCRIPTION OF THE DRAWINGS

FIG. 7 is a plan view of a tissue tack driver according to the present invention.

FIG. 8 is an end view detailing the head of the tissue tack driver of FIG. 7.

FIG. 9 is a cross-sectional plan view of a centering sleeve according to the present invention.

DETAILED DESCRIPTION OF THE PREFERRED EMBODIMENTS

Figure 1:
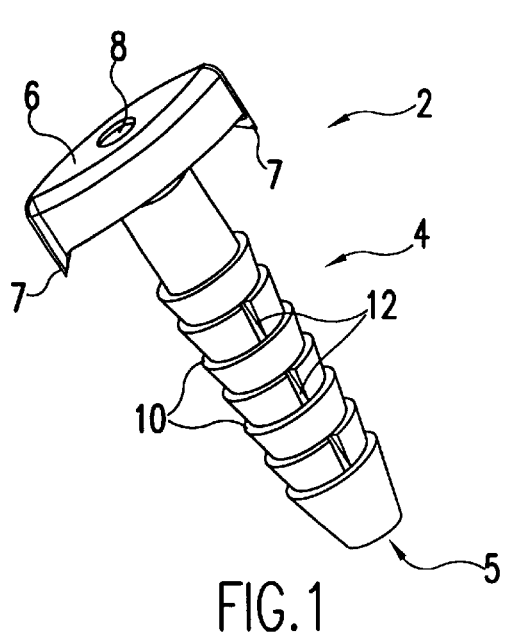
FIG. 1 is a perspective scale view of a bioabsorbable tissue tack with a straight head according to the present invention.
Figure 2:
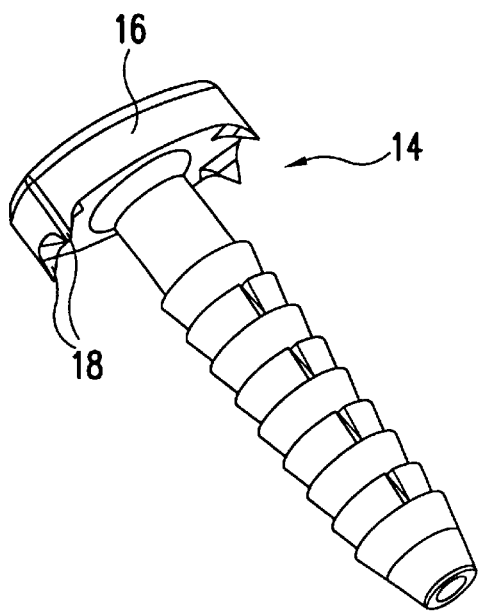
FIG. 2 is a perspective scale view of a bioabsorbable tissue tack with a straight head according to an alternative embodiment of the present invention.

A straight-headed bioabsorbable tissue tack 2 according to the present invention is shown in FIGS. 1–2. A tissue tack 22 having an angled head according to the present is shown in FIG. 3.

Referring to FIGS. 1–2, tissue tack 2 includes a cannulated shaft 4 with an oval-shaped cannulated head 6 disposed on the proximal end of the shaft. Tissue tack 2 has a blunt (i.e., flat) tip 5. In the embodiment of the invention shown in FIGS. 1–2, the head 6 is formed at a perpendicular angle with respect to the shaft 4. Anchoring barbs 7 are disposed on the longitudinal ends of oval-shaped head 6 and have pointed tips which extend distally toward the tip 5 of tack 2 to engage the labrum upon insertion. A cannula 8 extends continuously through the entire length of the tack 2, i.e., through both the head 6 and the tip 5 as well as the shaft 4. The cannula is 2.4 mm in diameter.

Tack 2 is provided with slotted ribs 10 formed circumferentially at least partially around and partially along the length of shaft 4. Ribs 10 have a truncated, conical shape, increasing in diameter toward the head of the tack at an angle of preferably 15° with respect to the longitudinal axis of tack 2, and reaching a major diameter of 3.0 mm. Slots 12 are formed in ribs 10 on alternating sides of shaft 4. The slots provide access for ingrowth of bony tissue for enhanced pullout strength.

Figure 3:
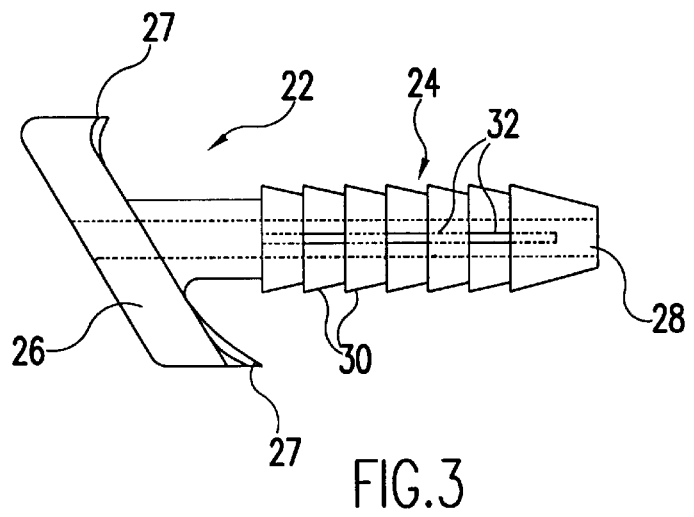
FIG. 3 is a plan scale view of a bioabsorbable tissue tack with an angled head according to the present invention.

FIG. 3 shows an embodiment in which a tissue tack 22 of the present invention is provided with an angled head. Specifically, tissue tack 22 has a cannulated shaft 24 provided with a cannulated oval-shaped head 26 disposed at an angle of 30° from the perpendicular with respect to the shaft 24. The 30° angle allows flush seating of the tack in the three o'clock to five o'clock positions, or the posterior superior labral positions, of the glenoid rim. As in the embodiment of FIGS. 1–2, a cannula 28 extends through the entire length of the tack 22, and tack 22 is provided with ribs 30 having slots 32 disposed on alternating sides of shaft 24.

The head is provided in 3.0 mm and 4.5 mm sizes (widths) to accommodate different anatomies. The 4.5 mm. tissue tack is preferably provided with four barbs (two at each end of the oval), whereas the 3.0 mm.: tissue tack has only two barbs (one at each end). In both cases, the major (end-to-end) length of the head is 7.0 mm, and the head is 1.65 mm thick. The working length of the implant, from the underside of the head to the distal tip, is 12.34 mm for the 3.0 mm head, and 14.7 mm for the 4.5 mm head. There is a smooth area of 3.07 mm from the most proximal edge of the most proximal rib to the underside of the head in both cases.

The preferred material for the tack is a non-crystalline, amorphous poly (L-lactide-co-D,L-lactide) 70%:30% (PLDLA) copolymer. This material reduces tissue reaction. The tack becomes encapsulated by fibrous tissue within six weeks after implantation, and generally degrades within 12 to 16 months. Although PLDLA is the most preferred material, other bioabsorbable materials known in the art can be utilized. As used herein, bioabsorbable is considered to be interchangeable with biodegradable, resorbable and absorbable to mean that the device can be absorbed by the body over time.

The tissue tack of the present invention is particularly well suited for reattachment of the glenoid labrum or inferior glenohumeral ligament in patients with primary or recurrent anterior dislocation or subluxation of the shoulder in association with adequate post-operative immobilization.

A preferred method of installing the tack is described in connection with performing an arthroscopic Bankart repair will now be described with reference to FIGS. 4–9.

Figure 4:
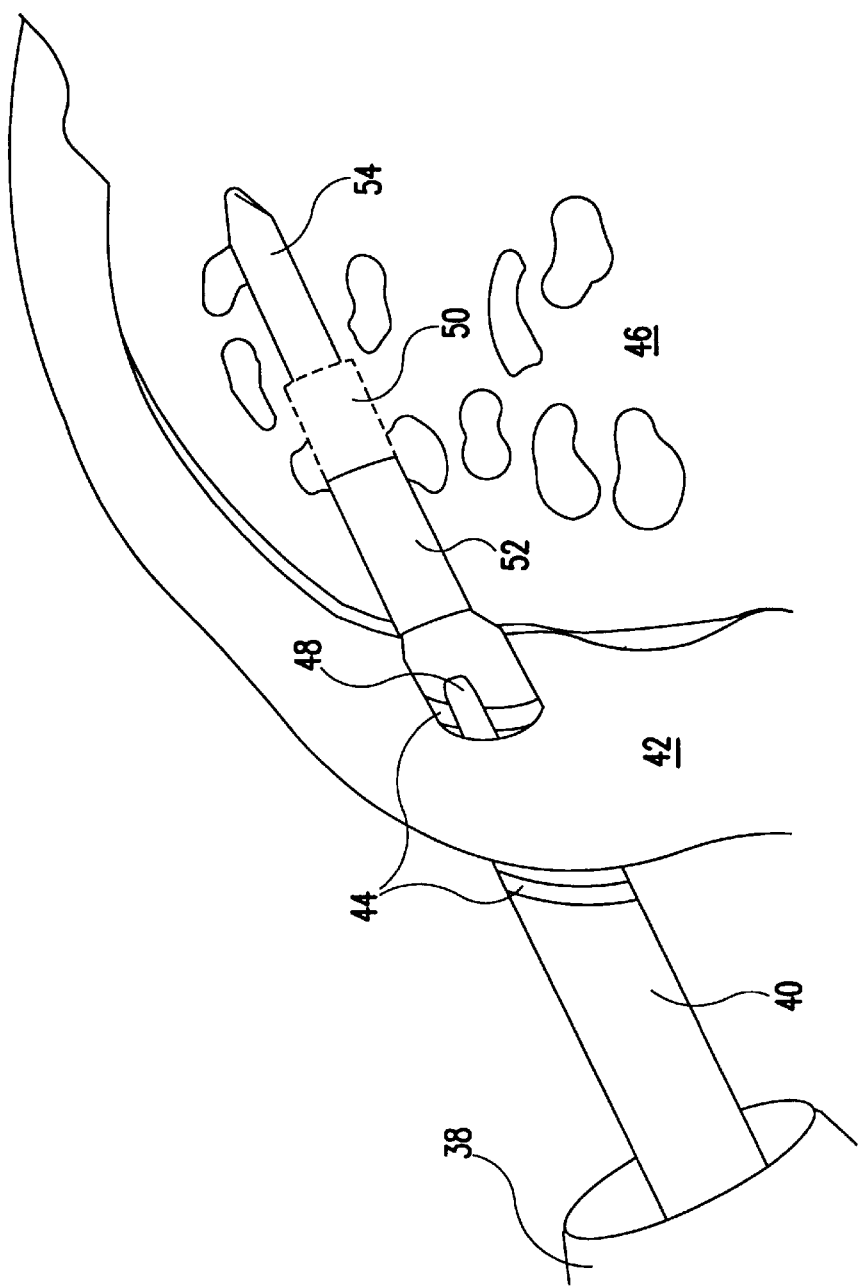
FIGS. 4–6 are schematic views illustrating a preferred method of shoulder repair according to the present invention.

Referring initially to FIG. 4, the arthroscopic procedure is performed within the shoulder through an access cannula 38. A 2.4 mm cannulated spear 40, such as that disclosed in pending U.S. Pat. No. 5,951,559, the disclosure of which is incorporated herein by reference, is inserted through the glenoid labrum 42 using an obturator (not shown). Laser markings 44 on the spear are referenced to confirm a perpendicular pilot hole for the straight or angled tissue tack. The labrum is shifted to the glenoid rim 46 using the spear.

The obturator is removed, leaving the spear in place holding the labrum proximate the glenoid rim. A non-cannulated 2.4 mm drill (not shown) is inserted into the spear. A window 48 in the spear provides arthroscopic control and visualization of the drill. A pilot hole 50 is drilled to a depth of 13 mm using a laser line (not shown) located distally on the drill as a depth stop reference.

The drill is removed, and a cannulated centering sleeve 52 (see also FIG. 9) is inserted into the spear (1 mm ID). The centering sleeve is pushed or tapped into the pilot hole 50. This allows central placement of a nitinol guide wire 54 into the pilot hole.

The 1 mm guide wire 54 is drilled or pushed, preferably using an insertion cap (not shown) such that the guide wire advances past the end of the centering sleeve up to a laser line on the guide wire. This locates the guide wire 5 mm further into cancellous bone to prevent the wire from coming out.

Once the guide wire 54 is secured in the base of the pilot hole 50, the centering sleeve 52 and the spear 40 are removed, leaving the guide wire 54 in position.

Figure 5:
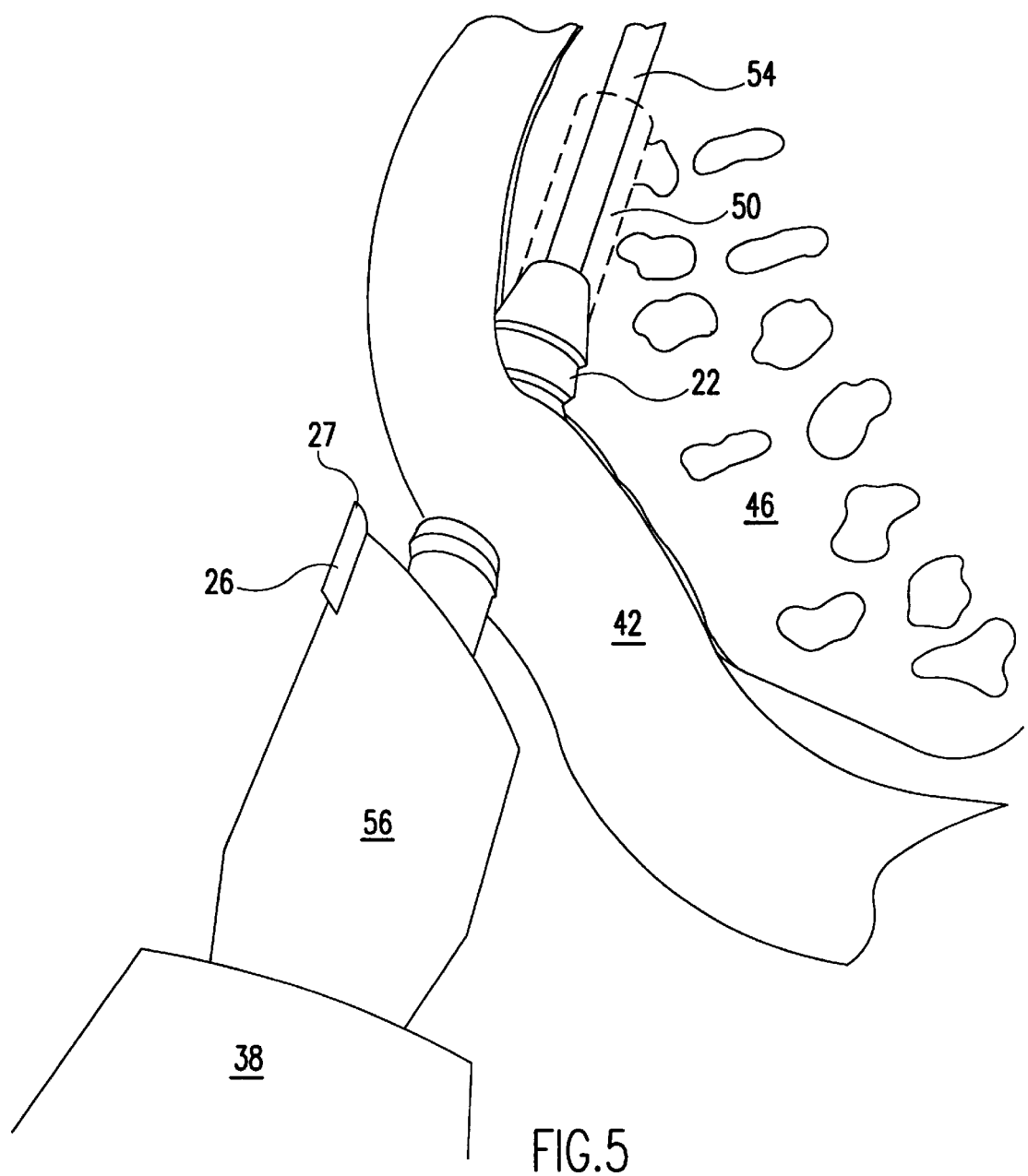

Referring to FIG. 5, a tissue tack 22 according to the present invention is installed over the guide wire 54. A cannulated tissue tack driver 56, having a 30° angled head as shown in FIG. 5, and described more fully below, is placed over the guide wire and engages the tack 22. Using the driver, the tack is advanced along the guide wire and into the pilot hole 50. Rotational adjustments can be made while the implant is partially seated, before barbs 27 tack into the labrum 42.

Figure 6:
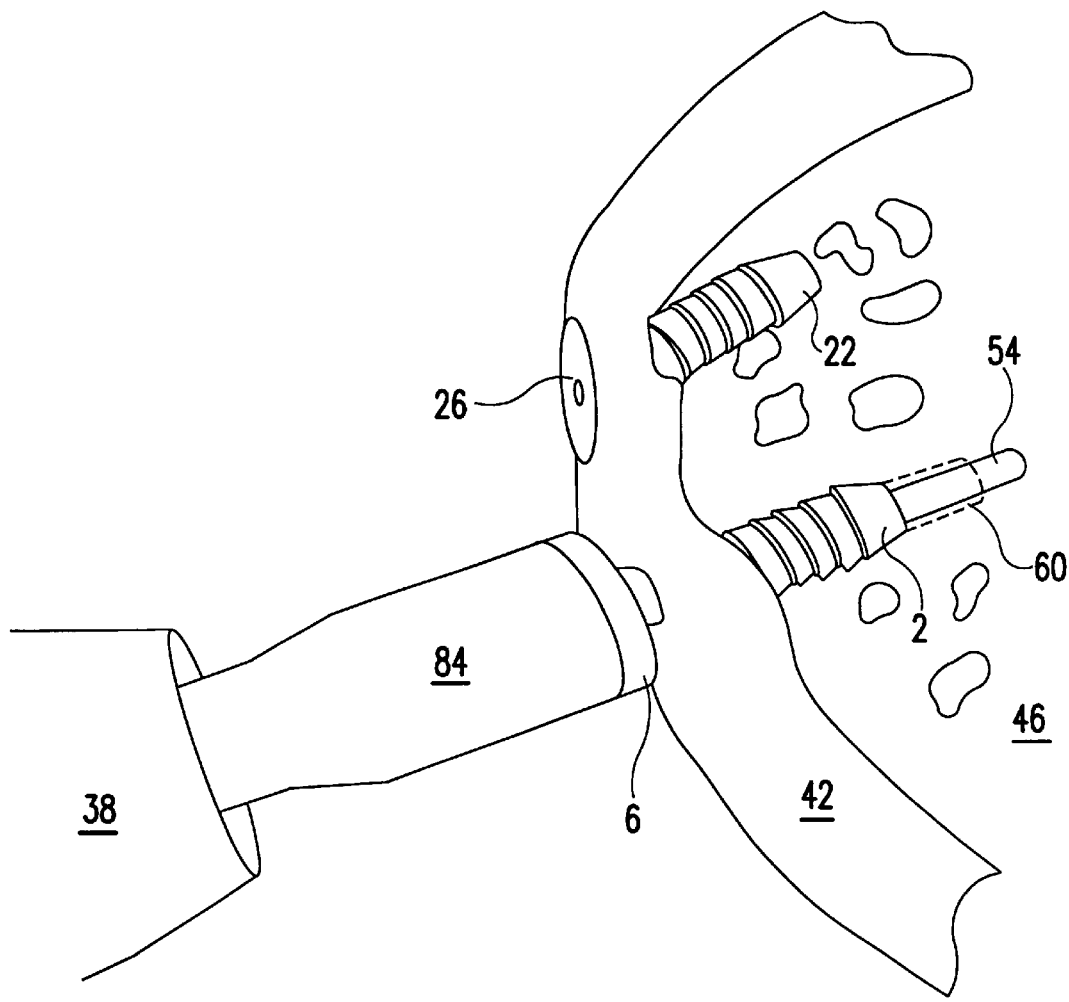

Referring to FIG. 6, further tissue tacks can be inserted in a similar manner to further secure the labrum. Accordingly, straight headed tack 2 is inserted into a second pilot hole 60 using a straight-headed driver 70 as shown in FIGS. 7 and 8. Driver 70 is similar to angle-headed driver 56 described above. The tissue driver has a cannulated handle 72 disposed on a cannulated shaft 74. The drive head 76 has a recessed portion 78 having a size and shape that corresponds to the head of the associated tissue tack. The recess 78 is flanked by two curved walls 80 separated by slots 82 engage either side of the tissue tack head and allow for proper alignment of the tissue tack with the glenoid rim during insertion, as noted above.

Once the tack has been properly aligned, a tamp 84 is driven with a mallet (not shown) to fully seat the tack with the long axis of the oblong head of the tissue tack aligned along the rim of the glenoid. The head of the tack is brought into flush proximity with the tissue surface, the tack slightly compressing the labrum. Tack 22 is shown having been seated using a tamp with an angled offset head. Placement of each tack is finalized by remove the guide wire and the driver.

Advantageously, the method and instrumentation of the present invention provide for placement of the guide wire after formation of the drill hole. This eliminates the possibility that the guide wire is inadvertently removed. In addition, the tack driver fully encloses the guide wire during insertion, thus eliminating the chance of surgical glove penetration. Repair of SLAP (superior labrum anterior posterior) lesions can be effected in a similar manner.

Although the present invention has been described in relation to particular embodiments thereof, many other variations and modifications and other uses will become apparent to those skilled in the art.

What is claimed is:

1. A bioabsorbable tissue tack for sutureless fixation of soft tissue to bone, comprising:
   a cannulated, non-expandable shaft having a distal end and a proximal end;
   a plurality of ribs formed circumferentially on the cannulated shaft and extending partially around the cannulated shaft to form slots in the ribs when splitting the cannulated shaft; and
   a cannulated, longitudinally oblong head as viewed along a central axis of the shaft is disposed on the proximal end of the shaft.

2. The bioabsorbable tissue tack according to claim 1, wherein the oblong head is disposed at an angle perpendicular to the central axis of the cannulated shaft.

3. The bioabsorbable tissue tack according to claim 1, wherein the oblong head is disposed at a non-perpendicular angle to the central axis of the cannulated shaft.

4. The bioabsorbable tissue tack according to claim 1, further comprising at least two barbs disposed on the head, at least one barb disposed at each longitudinal end of the oblong head, the barbs having respective pointed tips extending toward the distal end of the shaft for engaging the soft tissue upon insertion of the tack into bone.

5. The bioabsorbable tissue tack according to claim 1, wherein the ribs have a truncated conical shape with a surface sloped at an angle with respect to the longitudinal axis of the tack, the ribs have a major diameter greater than the diameter of the shaft of the tack, and the slots formed in the ribs do not extend into the shaft.

6. The bioabsorbable tissue tack according to claim 1, wherein a slot is formed in each of the ribs, such that the ribs extend less than completely circumferentially around the shaft of the tack, and slots in adjacent ribs are circumferentially offset.

7. A bioabsorbable tissue tack for sutureless fixation of soft tissue to bone, comprising:

a cannulated shaft having a distal end and a proximal end;

a plurality of ribs formed on the cannulated shaft and extending at least partially circumferentially around the cannulated shaft; and a cannulated oblong head disposed on the proximal end of the shaft, wherein a slot is formed in each of the ribs, such that the ribs extend less than completely circumferentially around the shaft of the tack, and the slots formed in the ribs are disposed alternately on opposing sides of the shaft.

8. A method for sutureless fixation of tissue to bone using a bioabsorbable tissue tack having a cannulated, non-expandable shaft with a distal end and a proximal end, at least one slotted rib formed on the cannulated shaft without splitting the cannulated shaft, and a cannulated, longitudinally oblong head as viewed along a central axis of the tack disposed on the proximal end of the shaft, the method comprising the steps of:

forming a hole in the bone; and installing the bioabsorbable tissue tack through the tissue and into the hole in the bone, wherein the tissue tack is secured in the hole by engagement of the at least one slotted rib without any expansion of the shaft, and wherein the tissue is fixed against the bone by the cannulated, longitudinally oblong head of the tissue tack.

9. The method of claim 8, wherein the step of installing the bioabsorbable tissue tack includes the steps of positioning a guide wire in the hole in the bone, disposing the cannulated shaft of the tissue tack over the guide wire, and advancing the tissue tack along the guide wire into the hole in the bone.

10. The method of claim 8, wherein the bone is a glenoid rim, and the method further comprises the step of aligning the oblong head along the glenoid rim.

* * * * *